United States Patent
Schug et al.

(10) Patent No.: US 10,987,463 B2
(45) Date of Patent: Apr. 27, 2021

(54) HANDPIECE FOR CLEANING WOUNDS

(71) Applicant: MEDAXIS AG, Baar (CH)

(72) Inventors: Martin Schug, Meggen (CH); Claudio Steiner, Baar (CH); Beat Widmer, Lucerne (CH)

(73) Assignee: MEDAXIS AG, Baar (CH)

( * ) Notice: Subject to any disclaimer, the term of this patent is extended or adjusted under 35 U.S.C. 154(b) by 0 days.

(21) Appl. No.: 14/912,772

(22) PCT Filed: Sep. 4, 2014

(86) PCT No.: PCT/EP2014/068853
§ 371 (c)(1),
(2) Date: Feb. 18, 2016

(87) PCT Pub. No.: WO2015/032866
PCT Pub. Date: Mar. 12, 2015

(65) Prior Publication Data
US 2016/0199566 A1 Jul. 14, 2016

(30) Foreign Application Priority Data
Sep. 6, 2013 (EP) .................................... 13183379

(51) Int. Cl.
*A61M 3/02* (2006.01)
*A61B 17/3203* (2006.01)
*A61B 17/32* (2006.01)

(52) U.S. Cl.
CPC ....... *A61M 3/0279* (2013.01); *A61B 17/3203* (2013.01); *A61M 3/0283* (2013.01); *A61B 2017/320004* (2013.01)

(58) Field of Classification Search
CPC .. A61M 3/0279; A61M 35/00; A61M 35/003; A61M 35/006; A61M 1/0064;
(Continued)

(56) References Cited

U.S. PATENT DOCUMENTS 3,818,911 A * 6/1974 Fournier ............. A61M 35/006
15/244.2
3,891,331 A * 6/1975 Avery .................... A45D 34/04
401/132
(Continued)

FOREIGN PATENT DOCUMENTS

CN 202113477 U 1/2012
EP 2251142 A1 11/2010
(Continued)

OTHER PUBLICATIONS

"Advantages of Polyethylene Pipe", 2020, Charter Plastics, URL http://www.charterplastics.com/advantages-of-polyethylene-pipe/ (Year: 2020).*
(Continued)

*Primary Examiner* — Laura A Bouchelle
(74) *Attorney, Agent, or Firm* — Marshall, Gerstein & Borun LLP

(57) ABSTRACT

A handpiece for cleansing wounds with a fluid jet includes a main body, which has a front end with an emergence opening for the emergence of the fluid jet, wherein a porous body is present on the front end, which porous body surrounds the emergence opening and protrudes beyond the latter in the direction of the fluid jet outlet and forms a space through which the fluid jet can pass unimpeded. The handpiece according to the invention combines the advantages of cleansing by a fluid jet with the advantages of mechanical cleansing and, at the same time, provides effective protection against aerosols.

13 Claims, 14 Drawing Sheets

(58) Field of Classification Search
CPC .......... A61B 17/3203; A61B 2217/005; A61B 2217/007
See application file for complete search history.

(56) References Cited

U.S. PATENT DOCUMENTS

| | | | |
|---|---|---|---|
| 5,037,431 A | 8/1991 | Summers et al. | |
| 5,380,300 A | 1/1995 | Pritchard et al. | |
| 6,099,494 A | 8/2000 | Henniges et al. | |
| 6,371,675 B1* | 4/2002 | Hoang | A45D 34/04 401/135 |
| 7,261,701 B2* | 8/2007 | Davis | A61M 35/006 401/135 |
| 2003/0049069 A1* | 3/2003 | Osei | A61M 35/006 401/205 |
| 2005/0276836 A1* | 12/2005 | Wilson | A61F 13/2051 424/422 |
| 2006/0264851 A1* | 11/2006 | Coleman | A61M 35/006 604/279 |
| 2007/0100300 A1 | 5/2007 | Hashemian | |
| 2008/0212411 A1 | 9/2008 | Polonio et al. | |
| 2009/0324319 A1* | 12/2009 | Houde | A61B 17/00491 401/138 |
| 2011/0066121 A1* | 3/2011 | Hoang | A45D 34/04 604/310 |
| 2014/0234004 A1* | 8/2014 | Thorpe | A45D 34/04 401/1 |

FOREIGN PATENT DOCUMENTS

| | | |
|---|---|---|
| JP | 2000-24073 A | 1/2000 |
| JP | 2002-514094 A | 5/2002 |
| WO | WO-82/03316 A1 | 10/1982 |
| WO | WO-97/48426 A2 | 12/1997 |
| WO | WO-2004/037095 A2 | 5/2004 |
| WO | WO-2008/074484 A1 | 6/2008 |
| WO | WO-2013/084945 A1 | 6/2013 |

OTHER PUBLICATIONS

International Search Report for International Application No. PCT/EP2014/068853, dated Nov. 18, 2014.
English Translation of the International Preliminary Report on Patentability for International Application No. PCT/EP2014/068853, dated Mar. 8, 2016.

* cited by examiner

HANDPIECE FOR CLEANING WOUNDS

CROSS-REFERENCE TO RELATED APPLICATION

The present application is the US national phase of International Patent Application No. PCT/EP2014/068853, filed Sep. 4, 2014, which application claims priority to Europe Application No. 13183379.0, filed Sep. 6, 2013. The priority application, EP 13183379.0, is hereby incorporated by reference.

TECHNICAL FIELD

Field of the Disclosure

The present invention relates to a handpiece, to a porous body, and to a method for cleansing wounds with a fluid jet.

Prior Art

Wound cleansing/debridement and wound rinsing/wound toilet refers to medical procedures for removing infected, damaged or dead (necrotic) tissue from ulcers, burns and other wounds or in cases of organ decay. There are numerous general approaches for cleansing wounds, e.g. mechanical sharp approaches using a scalpel or a sharp spoon, enzymatic or chemical, or autolytic, biosurgical, mechanical approaches using pads and a fluid jet.

EP 2 251 142 shows a handpiece for cleansing wounds with a high-pressure micro-fluid jet, wherein an emergence opening is arranged at the front end of the handpiece, through which a fluid jet can emerge.

Depending on the consistency, location, age and nature of the wound coating, the fluid jet has to be applied for different lengths of time and at different strengths in order to ensure sufficiently effective and sufficiently gentle detachment and removal of the wound coating while at the same time providing maximum protection of the tissue.

However, the fluid jet on its own is often not sufficient to achieve the desired cleansing effect. In this case, additional mechanical cleansing elements, e.g. pads, scalpels or sharp spoons, are used. This is awkward, however, since the operator needs a second hand for this purpose. This hand can be his own or that of an assistant. This complicates the wound cleansing. Moreover, this treatment in most cases causes the patient pain, and there is the danger of the tissue being unnecessarily damaged.

In case of cleansing wounds with a fluid jet, coatings or particles are removed from the wound, with aerosols being created in the process. It is important to ensure that the environment is contaminated as little as possible by these aerosols, since these constitute a danger to the patient or the operating staff. The prior art discloses numerous methods for reducing or preventing contamination of the environment by the aerosols. Such methods are e.g. returning the liquid, a shielding treatment tent with an exhaust lock, or the arrangement of the fluid jet and of the suction system in a covering hood. Said methods are complicated, since liquid not only has to be supplied, it also has to be returned.

Examples of wound cleansing devices involving a return of the liquid are disclosed in WO 2008/074284 and in WO 2004/037095.

SUMMARY OF THE INVENTION

It is therefore an object of the present invention to improve the cleansing of a wound and to prevent a spread of the aerosols.

The handpiece according to the invention for cleansing wounds with a fluid jet comprises a main body, which has a front end with an emergence opening for the emergence of the fluid jet. A porous body is present on the front end of the handpiece, which porous body surrounds the emergence opening and protrudes beyond the latter in the direction of the fluid jet outlet and forms a space through which the fluid jet can pass unimpeded.

The handpiece according to the invention combines the advantages of cleansing and treatment with a fluid jet, in particular a microfluidic jet, with the advantages of mechanical wound cleansing in a simple and cost-effective handpiece.

In the method according to the invention for cleansing wounds with such a handpiece, the wound is treated simultaneously by a fluid jet emerging from the handpiece and by a porous body arranged on the handpiece.

The pressure of the fluid jet can be set at different levels depending on the particular use. Thus, certain wounds can be treated with high pressure, whereas others can be treated with low pressure.

By simultaneously treating the wound with a fluid, in particular an aqueous solution or a treatment solution, e.g. a sterile saline solution, and mechanically treating the wound with the porous body, the tissue, in particular the vital and granulating tissue, is still protected optimally, compared to all the mechanically sharp methods. The combined application of the fluid jet and the mechanically acting porous body not only increases the cleansing action but additionally activates and stimulates the tissue. This promotes wound healing and accelerated wound closure, as a result of which the overall treatment costs are reduced.

The wound cleansing is improved and the treatment time shortened, while wound healing is additionally promoted. Protection is at the same time provided against aerosols, and it is therefore possible to dispense with the use of a cover or a protective tent, particularly when cleansing relatively small wounds.

The mechanical treatment can be targeted locally and can be applied only for as long as is strictly necessary. It is not necessary for the mechanical treatment to be applied throughout the treatment with the fluid.

Since the body is porous, aerosols that arise can be trapped in the body. The porous body can moreover take up fluids and tissue particles. An additional suction system can be omitted. Since the body surrounds the fluid jet and protrudes beyond the emergence opening, it offers optimal protection in the smallest possible space. The porous body can be configured with open pores on its outer circumference. However, its outer jacket can also be formed by a tight outer skin. For example, it can be covered by a layer of silicone or by a film. The outer skin can also be generated by a spray-on skin, by applying a varnish, by melting or by other known techniques.

It is possible to additionally provide a suction system. This additional suction system can increasingly carry away aerosols, fluids, biofilms or other substances present in the wound. If suction is provided, it takes place, in preferred embodiments, in the porous body. For this purpose, the porous body is preferably provided with the tight outer skin. The suction can take place through the pores that are present anyway in the porous body. In preferred embodiments, the porous body has suction channels with a larger diameter than the pores, wherein these suction channels preferably extend approximately parallel to the jet direction of the fluid jet. Preferably, the suction channels extend parallel to the jacket surface of the porous body. In further embodiments, radially extending suction channels are alternatively or additionally present which open into the space enclosed by the porous body, which space is also referred to as the first through-opening. By virtue of the suction, the porous body is saturated less quickly and the handpiece can be used for longer.

The fluid jet is preferably a microfluidic jet, in particular a high-pressure or low-pressure microfluidic jet. The pressure range is usually from 1 to 300 bar. The fluid jet is preferably a microfluidic jet, i.e. a fluid jet with a diameter of approximately 0.05 mm to 0.15 mm upon emergence from the emergence opening. The fluid jet is usually a single solid jet. However, it is also possible for a conical, hollow conical or flat jet to be used as a single or multiple jet.

In preferred embodiments, the emergence opening of the fluid jet is designed such that the jet extends approximately parallel to the longitudinal central axis of the porous body. In other preferred embodiments, it extends at an angle with respect to this longitudinal central axis. The angle is preferably approximately 45°. Compared with the emergence direction parallel to the central axis, this angled emergence direction results in a different treatment action and abrasion action on the wound surface. Thus, a fluid jet emerging at an angle of 45° with respect to the longitudinal central axis, and thus also striking the wound surface at this angle, has a peeling action.

The porous body can be designed in one piece. It can also be composed of several subsidiary bodies which are arranged at the front end of the handpiece and together form a closed body surrounding the emergence opening. The porous body can also have interruptions. However, it is preferably mostly or completely closed, such that the emergence opening is surrounded seamlessly by the porous body.

The porous body is preferably made of a material like a sponge, fleece or knit. The material is preferably synthetic. These materials have favorable mechanical properties for wound cleansing. They are sufficiently firm to have the required inherent stability, but they are flexible enough not to cause any injuries upon contact with the wound. On account of the porosity, they are also distinguished by an increased surface area, which favors the cleansing action.

The porous body can be provided with a coating having a disinfecting action.

Preferably, the porous body can be arranged with an inner surface on the front end of the handpiece. Additionally or alternatively, it can be arranged on the handpiece via a rear face directed toward the front end of the handpiece. If only the inner surface is used for the arrangement, the porous body can, for example, be pushed over the front end of the handpiece. The use of the rear face of the porous body as a contact surface increases the overall surface area, which is advantageous, for example, in the case of a cohesively bonded connection.

The front end of the handpiece is preferably transparent, which permits a better view of the wound that is to be cleaned.

The porous body is preferably arranged in a fixed manner or releasably on the front end of the handpiece. A releasable connection between the front end of the handpiece and the porous body affords the advantage that the porous body is exchangeable and can be disposed of after use, or different porous bodies can be used for different applications. For example, different porous bodies can be used with the same handpiece, said porous bodies differing from one another in terms of porosity, shape, material and/or degree of abrasion.

However, the porous body can also be connected to the front end of the handpiece with a form fit or force fit. This simplifies production, since it is possible to dispense with complicated connections.

Preferably, an outer contour of the front end is larger than the inner contour of the porous body containing the inner surface. In this way, the porous body can be arranged with a clamping action on the front end of the handpiece. Preferably, however, the porous body is movable, which makes it possible to adjust the distance from the emergence opening to a contact surface of the porous body. Thus, for example, it can be pushed down toward the wound to permit the mechanical treatment of the wound and, when the fluid jet is used on its own, it can be withdrawn from the area of contact with the wound. It is thus possible to set a distance that is adapted specifically to the patient or to the wound.

Preferably, the front end of the handpiece has a recess for receiving the porous body. This makes it easier to fit the porous body on the front end of the handpiece. In the case of a fixed connection, a recess makes positioning easier and increases the contact surface area between the front end of the handpiece and the porous body. In the case of a releasable connection, a recess permits the formation of a form-fit connection.

Preferably, the porous body can be arranged on the front end of the handpiece by means of an adapter. The adapter has the advantage that it is easily detachable together with the porous body. Thus, a form-fit or force-fit connection can be realized between the front end of the handpiece and the adapter. The adapter is preferably configured such that it completely covers the front end of the handpiece except for an emergence opening. This affords the advantage that the front part is not contaminated by the aerosols that arise. However, the adapter can also be configured such that an area of the front end of the handpiece is accessible from the front.

The body preferably has a substantially hollow cylindrical, conical or polyhedral shape. Cylindrical and conical shapes are easier to produce and assemble and are therefore more cost-effective. By contrast, polyhedral shapes can be specifically configured, for example in order to form areas of different stiffness in the porous body.

The porous body preferably has a contact area for contact with a wound, which contact area extends substantially perpendicularly with respect to the direction of the fluid jet outlet.

The porous body preferably has a contact area, for contact with a wound, that extends substantially at an angle other than 90° with respect to the direction of the fluid jet outlet. When, during cleansing, the contact area is then placed onto the wound to be cleaned, the fluid jet strikes the surface to be cleaned and does so at an angle. The angle between the fluid jet and the perpendicular on the surface to be cleaned can be 0° to 90°. For example, porous bodies with an angle of 5°, 10°, 15°, 30°, 45°, 60° or 75° can be made available to the user.

The porous body preferably has, in the contact area, an outwardly directed, circumferential front collar. The collar increases the stiffness of the porous body in the contact area. It likewise increases the area of the wound to be cleaned that can be covered by the porous body.

In another preferred embodiment, the porous body has a circumferential rear collar, which is inwardly directed in a rear area, for engaging in a corresponding recess of the front end. In this way, a releasable connection which can be easily produced is realized between the two elements. The shape of the collar must be such that a substantially form-fit connection can be realized. The collar can, for example, have a circular, polyhedral or helical shape. However, it can also be composed of several collars arranged in series.

A porous body as described above is preferably to be used with a handpiece as described above. The handpiece and the porous body form a coordinated unit. The handpiece preferably has a nozzle, which forms the emergence opening. Preferably, the handpiece, and in particular the front end of the handpiece, is stiff.

The porous body has an adapter for connection to the handpiece. Preferably, the adapter is connected cohesively to the porous body and forms an exchangeable unit with the latter. Different units can thus be quickly and easily exchanged.

The porous body preferably has a first through-opening, which forms the space. In this way, the fluid jet is not deflected by the porous body.

Further embodiments are set forth in the dependent claims.

BRIEF DESCRIPTION OF THE DRAWINGS

Preferred embodiments of the invention are described below with reference to the drawings, which serve only for illustrative purposes and are not to be interpreted as limiting the invention. In the drawings.

DESCRIPTION OF PREFERRED EMBODIMENTS

Figure 1:
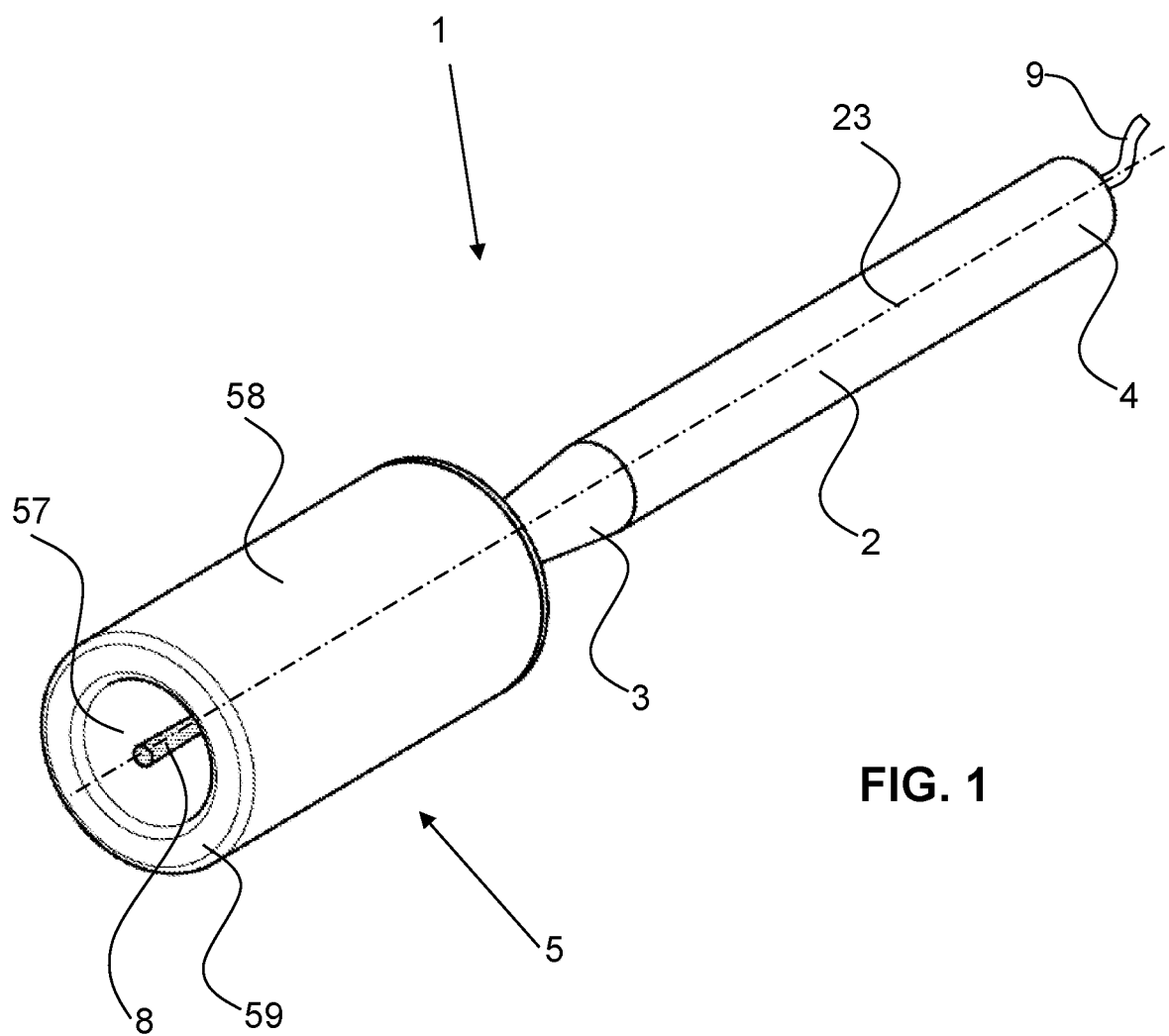
FIG. 1 shows a perspective view of a first embodiment of a handpiece according to the invention, with fluid jet.
Figure 2:
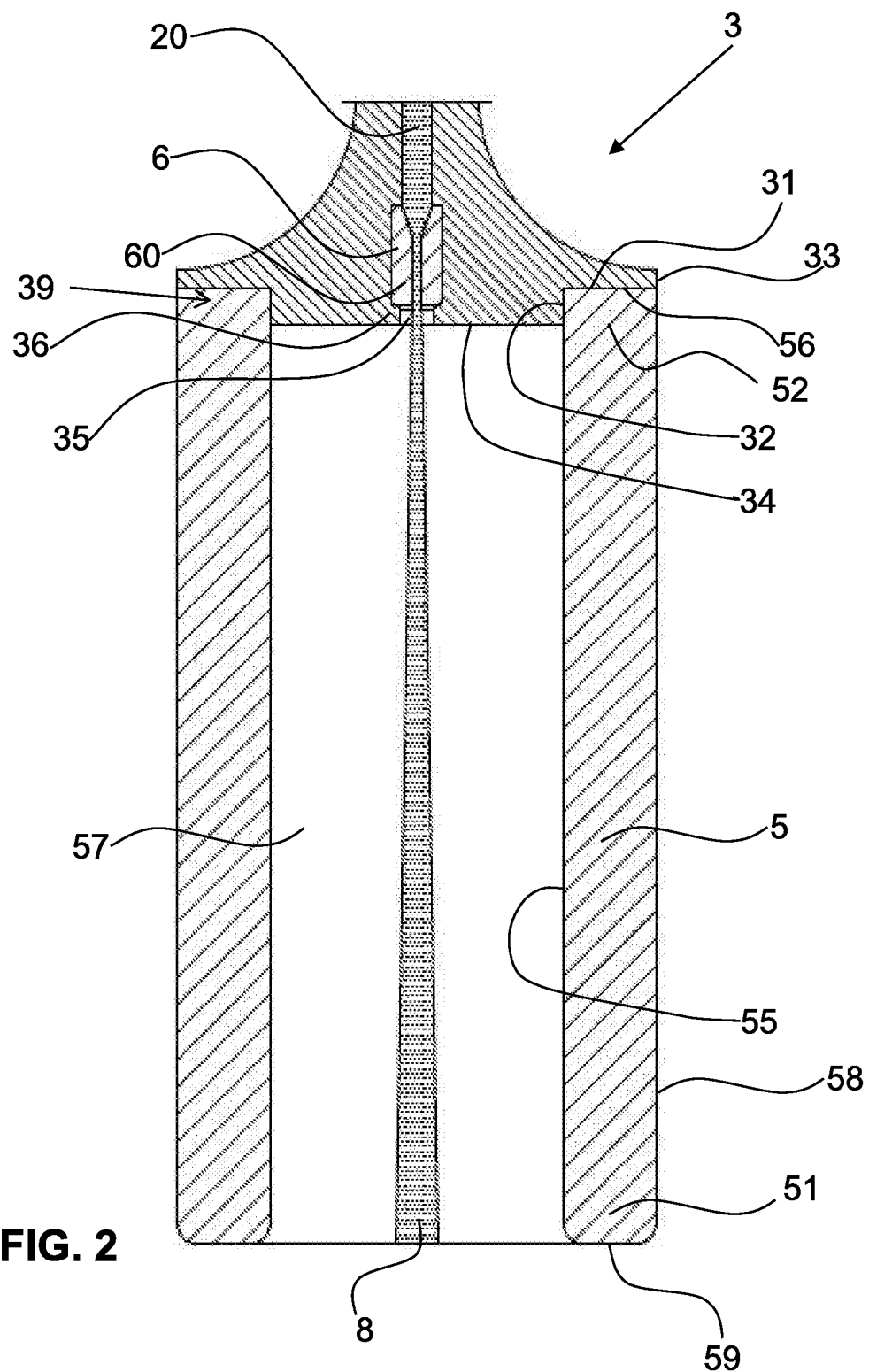
FIG. 2 shows a central sectional view of the front end of the handpiece with a porous body according to FIG. 1, with fluid jet.

FIG. 1 shows a perspective view of a first embodiment of a handpiece 1 according to the invention with fluid jet 8, while FIG. 2 shows a central sectional view of the front end 3 thereof. The handpiece 1 has a substantially cylindrical main body 2 for holding in one hand, with a front end 3 and a rear end 4. The front end 3 is preferably transparent. The front end 3 has an emergence opening 35 for the emergence of the fluid jet 8. The emergence opening 35 is arranged centrally in a first front face 34 of the handpiece 1. The handpiece 1 is designed in such a way that the fluid jet 8 flows out of the emergence opening 35 substantially collinearly with respect to the central axis 23 of the main body 2.

A porous body 5 provided for gentle mechanical wound cleansing, and acting as a protective sleeve, is arranged at the front end 3. The porous body 5 has substantially the shape of a hollow cylinder with a first through-opening 57, which forms a space. With its rear area 52, it surrounds the emergence opening 35 and protrudes beyond the latter in the direction of the fluid outlet. The first front face 34 has a recess 39 with a first axial limit surface 31 and a first radial limit surface 32 for receiving the porous body 5. The porous body 5 bears with an inner surface 55 on the first radial limit 32 of the front end 3 and bears with a rear face 56 on the first axial limit 31 of the front end 3. An outer surface 58 of the porous body 5 is designed flush with a first radial outer surface 33 of the front end 3.

In this illustrative embodiment, there is preferably a cohesively bonded connection between the front end 3 and the porous body 5. However, a force-fit and/or form-fit connection is also possible.

On a face lying opposite the rear area 52, the porous body 5 has a contact area 51. The latter has a contact surface 59 which is parallel to the first front face 34 of the front end 3 and which adjoins the inner surface 55 and the outer surface 58. The transitions between the contact surface 59 and the inner surface 55 and outer surface 58 are preferably rounded.

The front end 3 comprises a centrally arranged fluid channel 20 and, flush with the latter, a nozzle 6, which is in turn flush with the emergence opening 35. The substantially cylindrical nozzle 6 is received in a known manner in the front end 3 of the handpiece 1, and its position in the jet direction is defined by a front abutment 36. The nozzle 6 has a nozzle channel 60 arranged centrally therein. The design of this channel defines the emergence geometry of the fluid jet 8.

FIG. 1 further shows that the rear end 4 has a fluid line 9, wherein the fluid line 9 ensures the supply of fluid to the handpiece 1. The following embodiments of the handpiece 1 according to the invention likewise have a fluid line 9 at the rear end 4. However, it is not shown.

Figure 3:
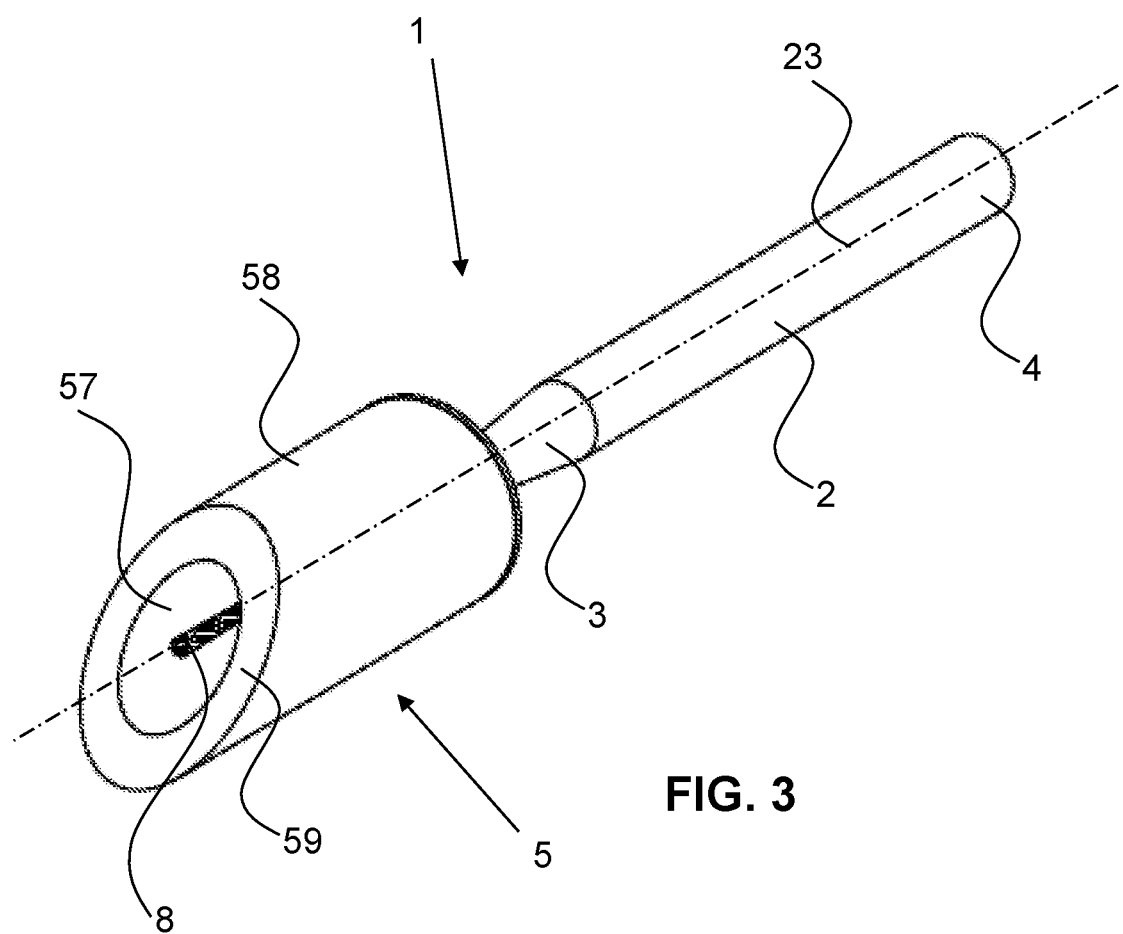
FIG. 3 shows a perspective view of a second embodiment of a handpiece according to the invention, with fluid jet.
Figure 4:
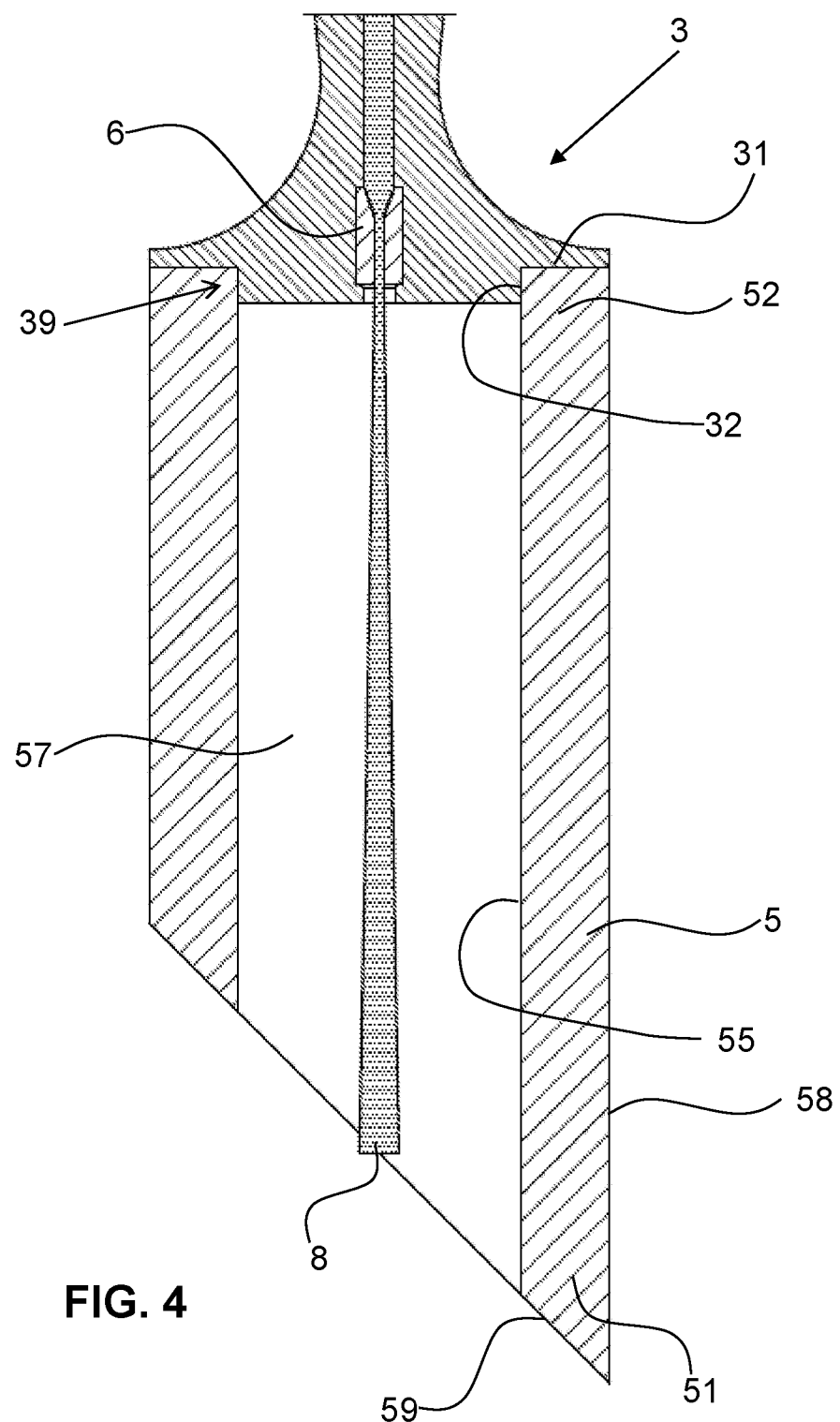
FIG. 4 shows a central sectional view of the front end of the handpiece with a porous body according to FIG. 3, with fluid jet.

FIG. 3 shows a perspective view of a second embodiment of the handpiece 1 according to the invention with a fluid jet 8, while FIG. 4 shows a central sectional view of the front end 3 thereof. The first and second embodiments are largely identical. In contrast to the first embodiment, the porous body 5 of the second embodiment has a beveled contact area 51 and preferably has sharp-edged transitions between the contact surface 59 and the inner surface 55 and outer surface 58. The bevel is shown by the fact that the contact surface 59 extends at an angle other than 90° with respect to the jet direction. The angle depicted corresponds to approximately 45°.

Figure 5:
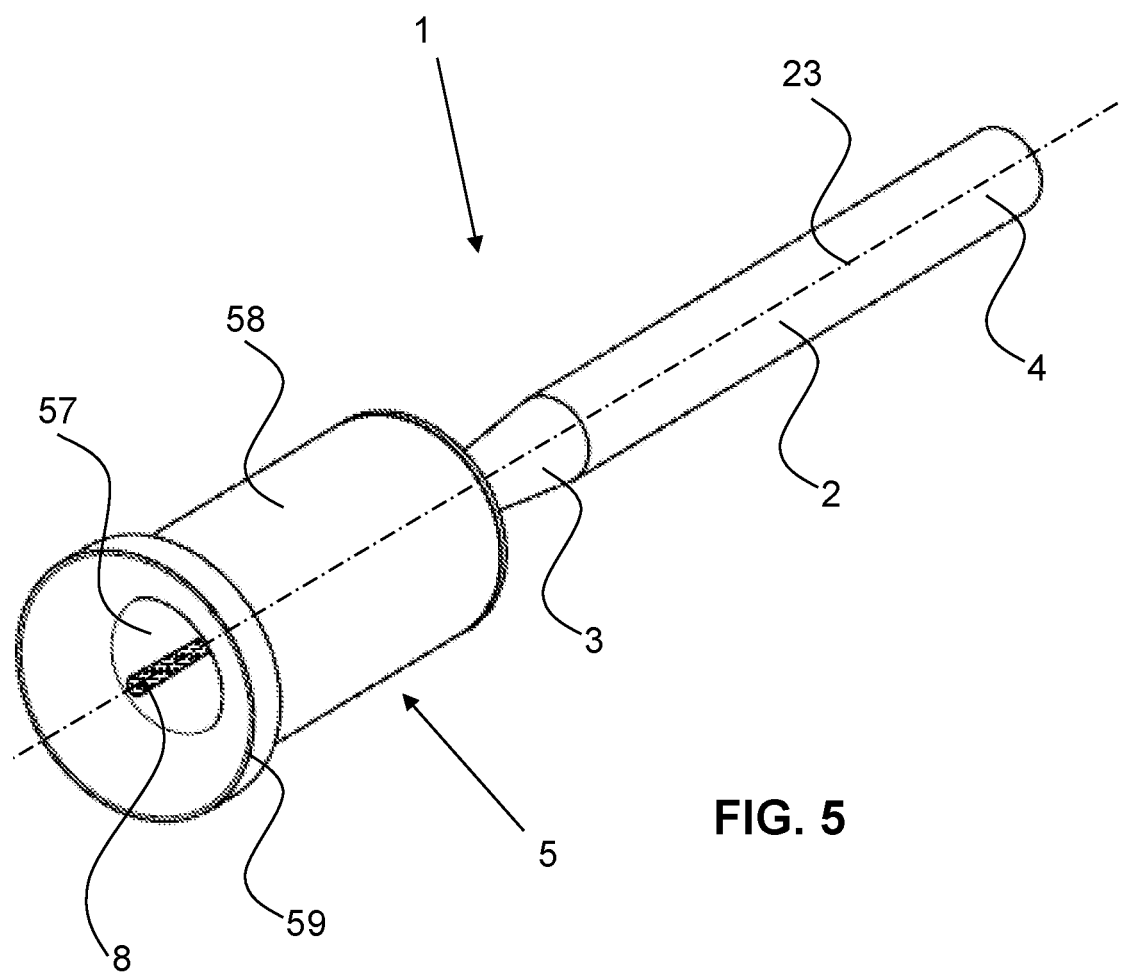
FIG. 5 shows a perspective view of a third embodiment of a handpiece according to the invention, with fluid jet.
Figure 6:
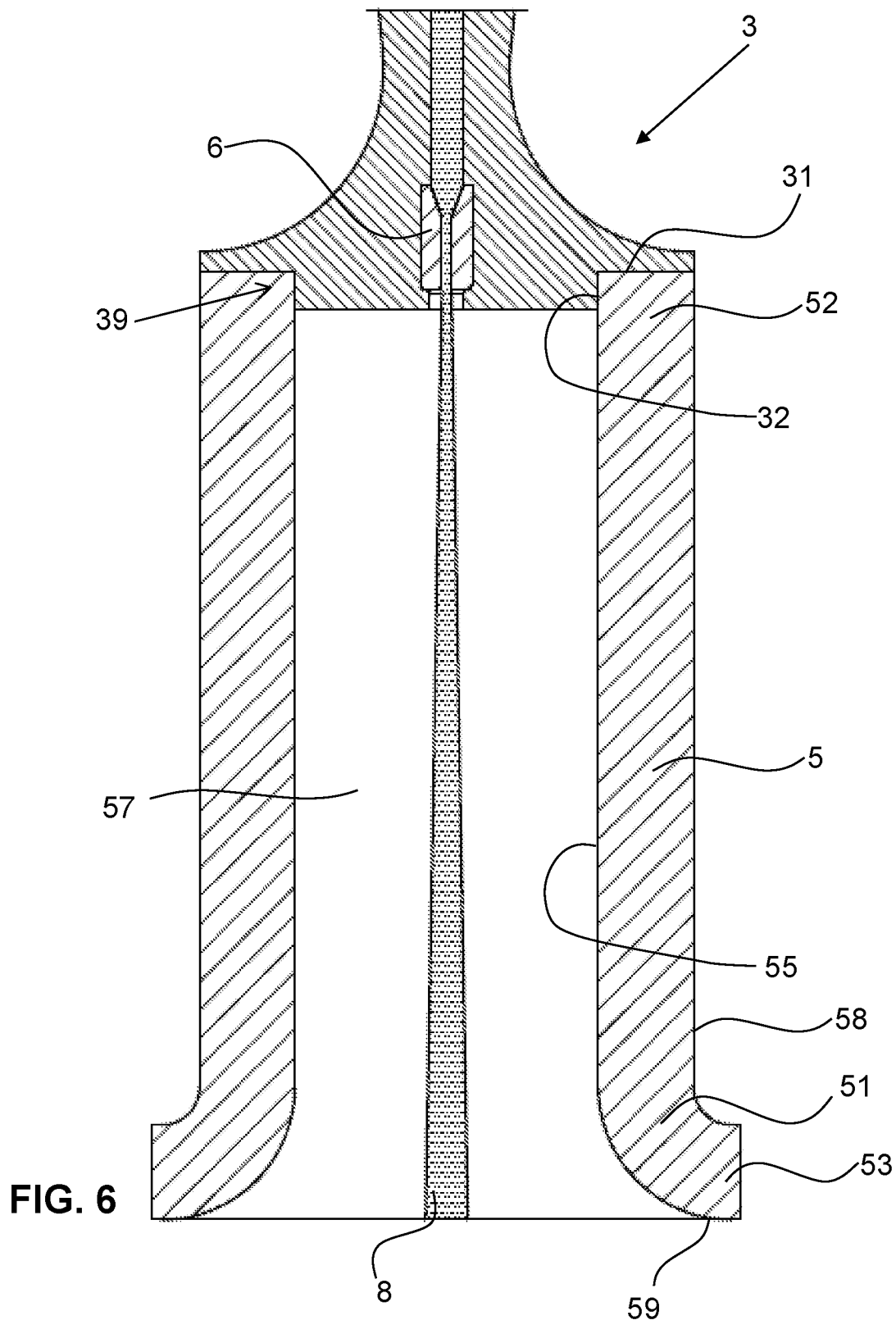
FIG. 6 shows a central sectional view of the front end of the handpiece with a porous body according to FIG. 5, with fluid jet.

FIG. 5 shows a perspective view of a third embodiment of a handpiece 1 according to the invention with a fluid jet 8, while FIG. 6 shows a central sectional view of the front end 3 thereof. The first, second and third embodiments are largely identical. In contrast to the first two embodiments, the porous body 5 of the third embodiment has an outwardly directed front collar 53 in the contact area 51. The transition between the front collar 53 and the inner surface 55 and outer surface 58 is rounded. The wall thickness of the porous body 5 is constant along its cylindrical length and does not change in the area of the front collar 53. The rounding of the transition from the contact surface 59 to the inner surface 55 creates a funnel-shaped area in the first through-opening 57 in the contact area 51.

Figure 7:
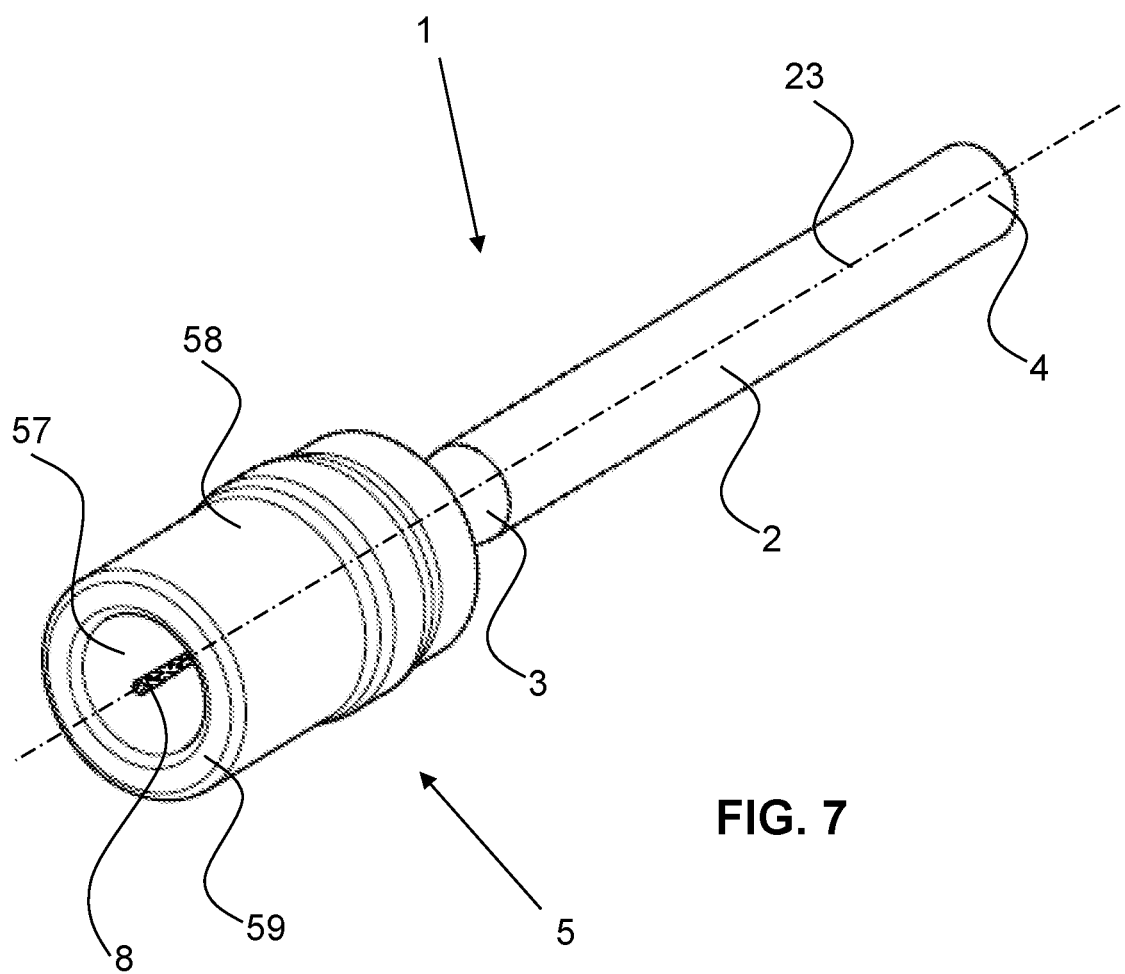
FIG. 7 shows a perspective view of a fourth embodiment of a handpiece according to the invention, with fluid jet.
Figure 8:
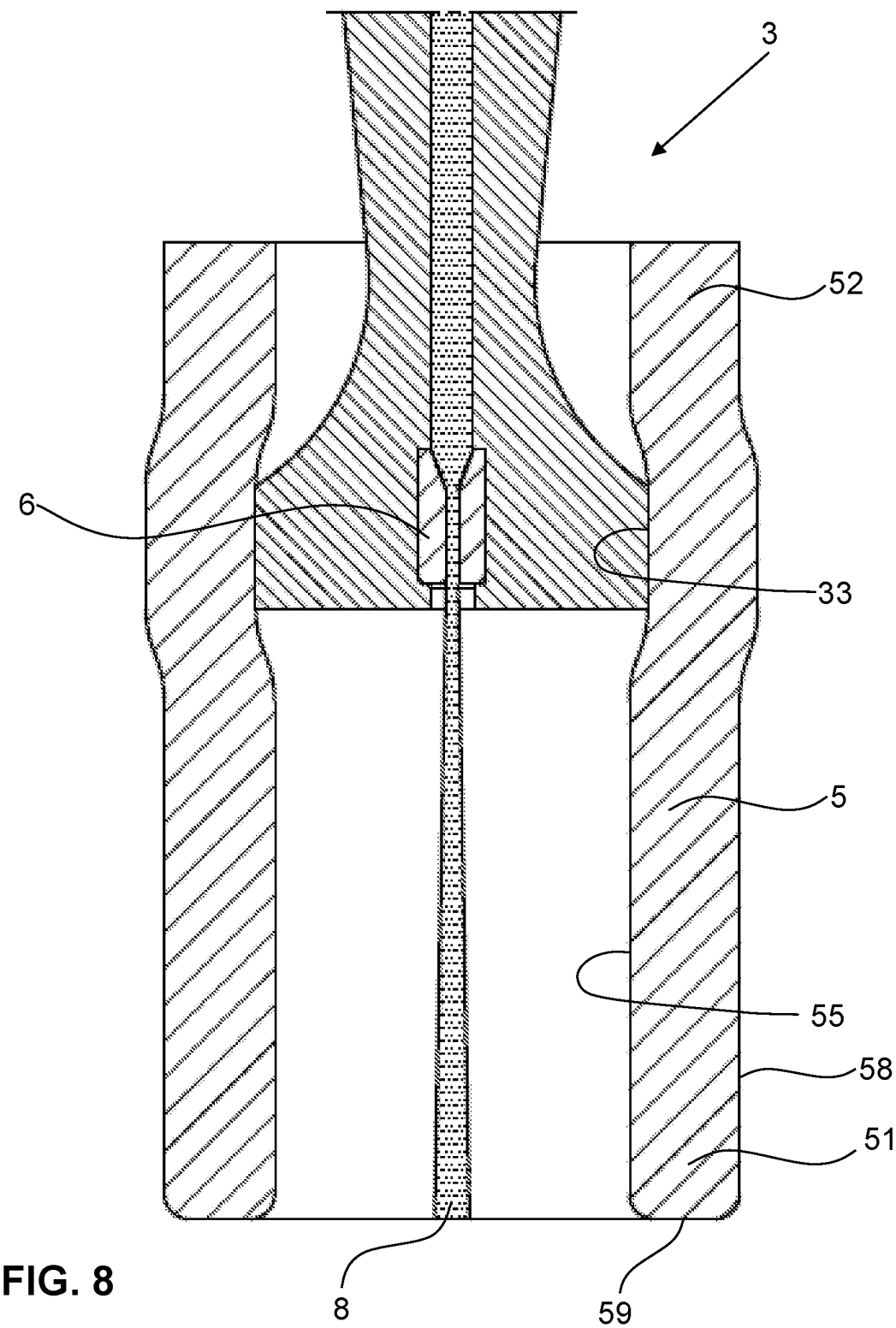
FIG. 8 shows a central sectional view of the front end of the handpiece with a porous body according to FIG. 7, with fluid jet.

FIG. 7 shows a perspective view of a fourth embodiment of a handpiece 1 according to the invention with a fluid jet 8, while FIG. 8 shows a central sectional view of the front end 3 thereof. The porous body 5 has largely the same design as that of the first embodiment. However, the front end 3 of the fourth embodiment is different than that of the first embodiment. However, the front end 3 is preferably likewise transparent. The first radial outer surface 33 of the front end 3 is dimensioned such that it can be inserted into the first through-opening 57. The diameter of the first radial outer surface 33 is preferably slightly larger than the internal diameter of the first through-opening 57. The inner surface 55 is movable and arranged clamped on the first radial outer surface 33 of the front end 3. The distance between the emergence opening 35 and the contact surface 59 is adjustable by a relative movement between the front end 3 and the porous body 5.

Figure 9:
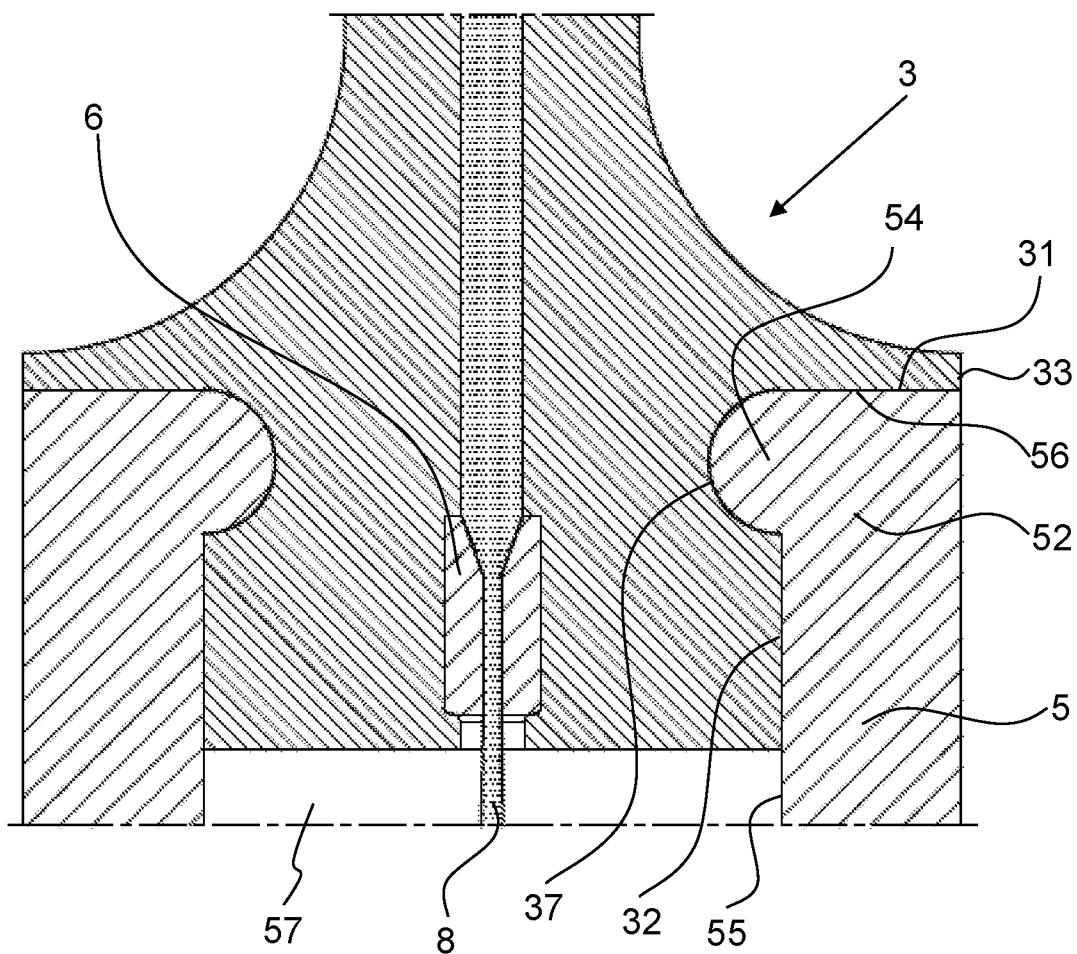
FIG. 9 shows a central sectional view of the front end of a handpiece with a porous body according to a further embodiment.

FIG. 9 shows a central sectional view of the front end of a handpiece with porous body according to a further embodiment. FIG. 9 basically shows an alternative releasable connection between the front end 3 and the porous body 5, as would be able to be used in the handpiece 1 of a first, a second or a third embodiment. Advantageously, the front end 3 of this embodiment is likewise transparent. In the rear area 52, the porous body 5 has an inwardly directed, circumferential rear collar 54, which engages in a corresponding recess 39 in the front end 3 and forms a releasable connection 37 with the latter. A collar 54 is shown that has a cross section in the shape of a semicircle. The inner surface 55 of the porous body 5 is in releasable contact with the first radial limit 32 of the front end 3, and the rear face 56 of the porous body 5 is in releasable contact with the first axial limit 31 of the front end 3. By pulling on the porous body 5 in the jet direction, said porous body 5 can be removed from the front end.

Figure 10:
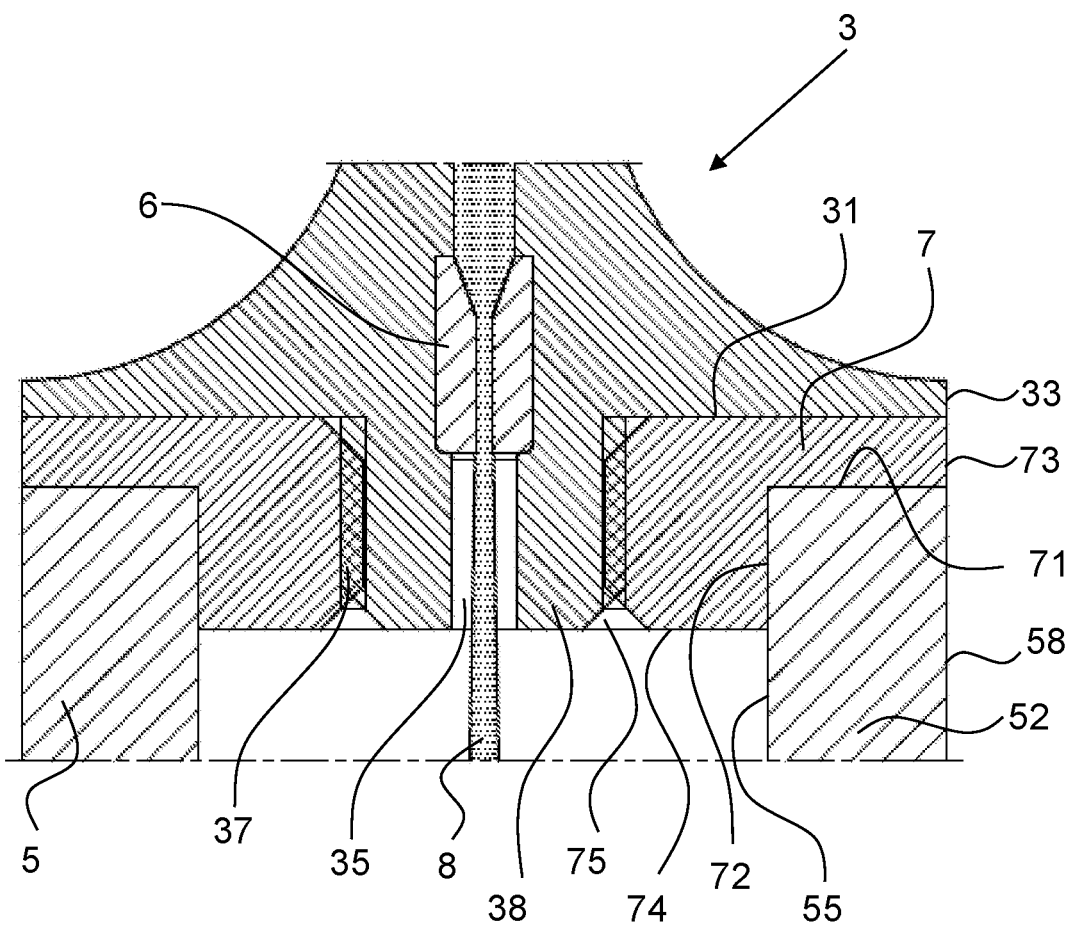
FIG. 10 shows a central sectional view of the front end of a handpiece with a porous body according to a further embodiment.

FIG. 10 shows a further alternative to the releasable connection of the front end 3 to the porous body 5. The porous body 5 is connectable releasably to the front end 3 by means of an adapter 7. The adapter 7 and the front end 3 are preferably transparent. The front end 3 has a connecting pin 38, which is arranged centrally and surrounds the emergence opening 35. The adapter has a central second through-opening 75, which is oriented coaxially with the porous body 5. The connecting pin 38 and the second through-opening 75 together form a releasable connection 37, here shown in the form of a screw connection. A second front face 74 of the adapter 7 has a cutout with a second axial limit surface 71 and a second radial limit surface 72 for receiving the porous body 5. The porous body 5 bears via the inner surface 55 on the second radial limit 72 of the adapter 7 and bears via the rear face 56 on the second axial limit 71 of the adapter 7. The outer surface 58 of the porous body 5 is flush with a second radial outer surface 73 of the adapter 7.

Figure 11:
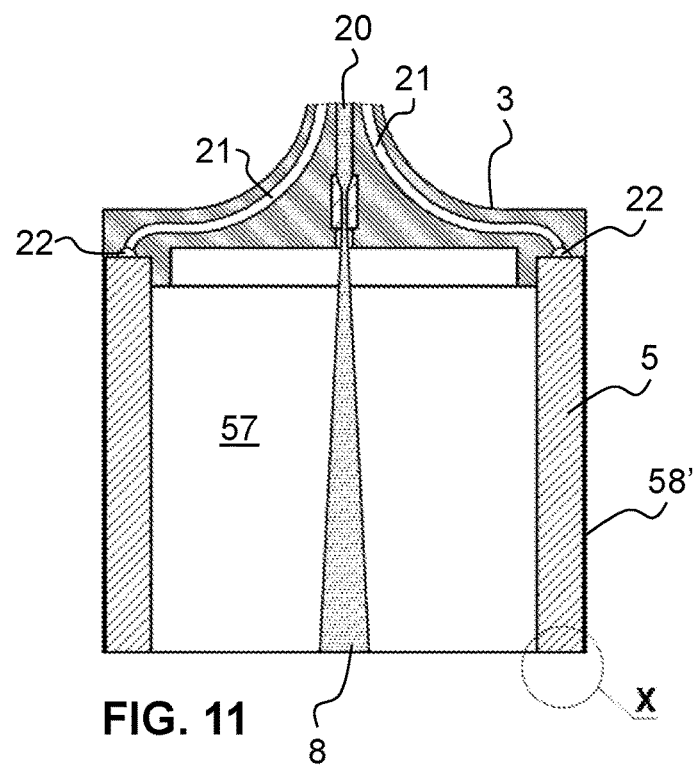
FIG. 11 shows a central sectional view of a further embodiment according to the invention with suction.
Figure 12:
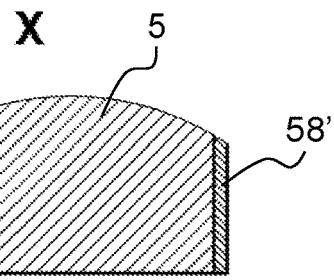
FIG. 12 shows an enlarged view of a detail X according to FIG. 11.

An embodiment with a tight outer skin 58' and with a suction system is provided in FIG. 11. The tight outer skin 58' can be seen clearly in FIG. 12. It is preferably a layer which is applied to the porous body and which completely surrounds the outer circumference of the porous body 5 and provides an airtight and liquid-tight seal from the outside. It preferably covers the jacket area but leaves the lower face 59 of the porous body 5 free, the lower face therefore being configured in an open-pored manner. In alternative embodiments, this lower face is also covered.

The main body 2 has at least one suction channel dividing up in the front end 3 of the handpiece 1 into suction channels 21 and leading to the upper face of the porous body. Several suction channels 21 may already be present in the main body 2 and, for example, do not divide up any further. An annular distributor channel 22 is preferably present on said face, said distributor channel 22 being open toward the porous body 5, or open in sections, and ensuring that the underpressure applied via the suction channel is distributed uniformly across the front circumference of the porous body 5. In this embodiment, the suction takes place via the pores of the porous body 5.

Figure 13:
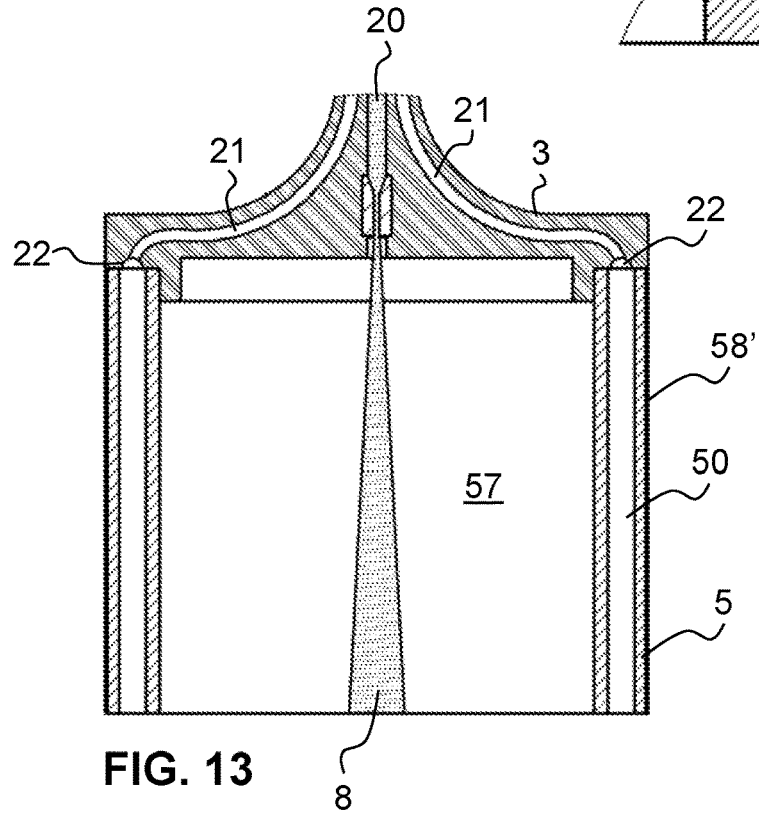
FIG. 13 shows a central sectional view of a further embodiment according to the invention with suction.

In the embodiment according to FIG. 13, the porous body 5 has several suction channels 50 preferably distributed uniformly about its circumference. These suction channels 50 extend parallel to the jacket surface and/or parallel to the jet direction of the fluid jet 8. The suction channels 50 preferably extend rectilinearly and have a larger diameter than the average pore size of the porous body 5. Their diameter is preferably many times the average pore size. These vertical suction channels 50 preferably extend as far as the lower face 59 of the porous body and are therefore open at the bottom. However, they can also terminate farther up or can be closed by the tight outer skin.

Depending on the embodiment, the distributor channel 22 is open exclusively toward these suction channels 50 or it also opens toward other locations of the face of the porous body. This embodiment with the suction channels 50 has the advantage that the suction still functions even when the porous body 5 is strongly saturated, since blocking of the pores is prevented.

Figure 14:
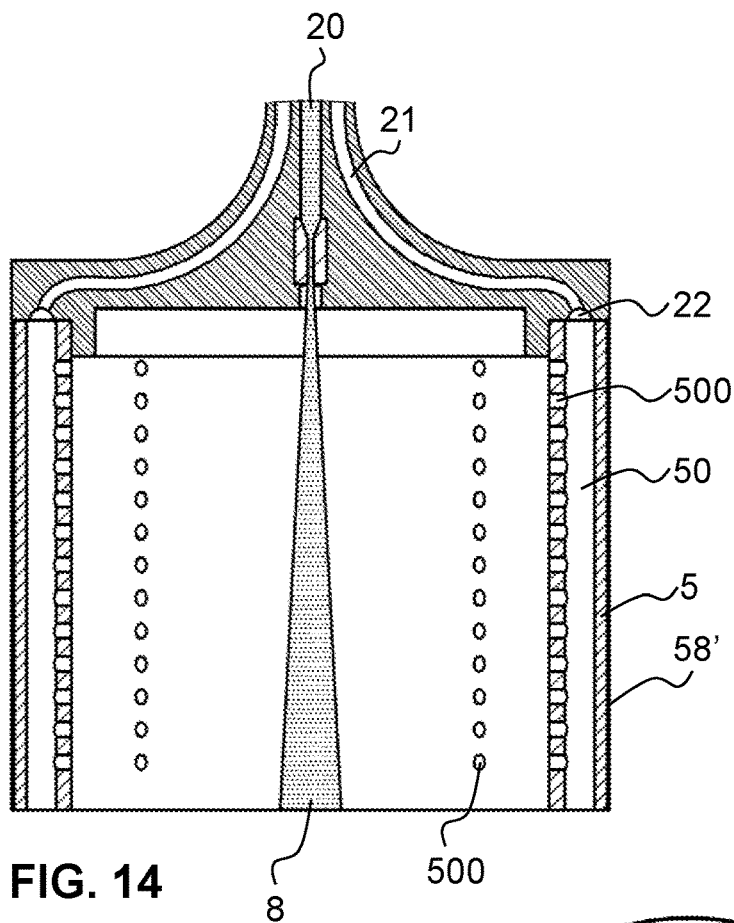
FIG. 14 shows a central sectional view of a further embodiment according to the invention with suction.
Figure 15:
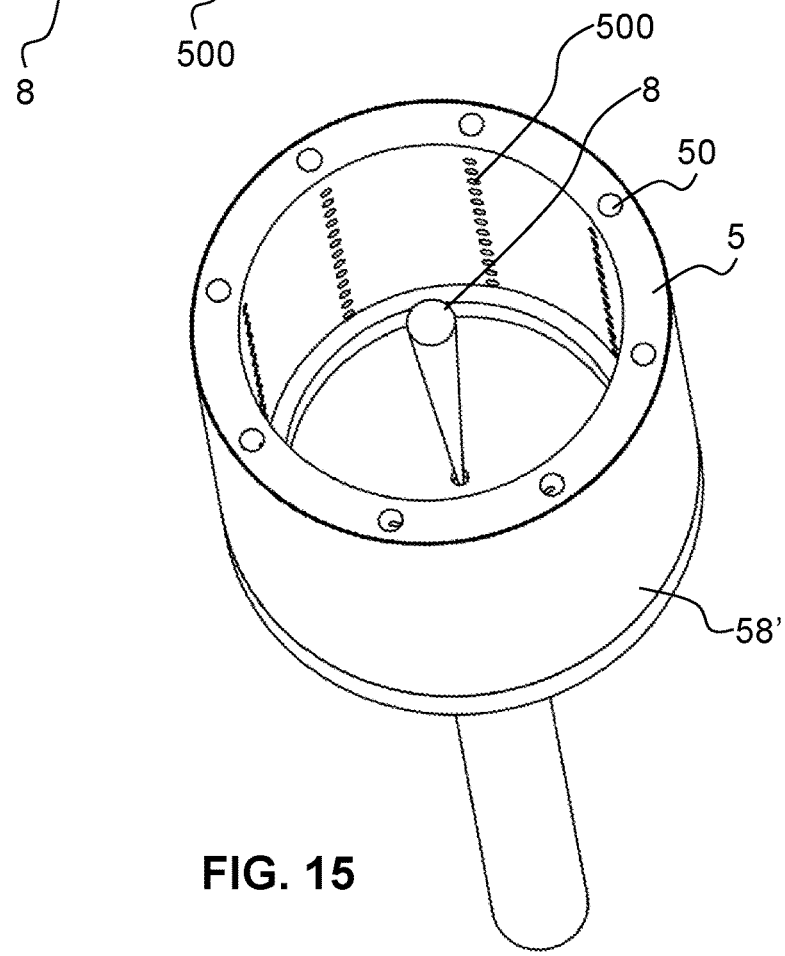
FIG. 15 shows a perspective view of the embodiment according to FIG. 14 from below.
Figure 19:
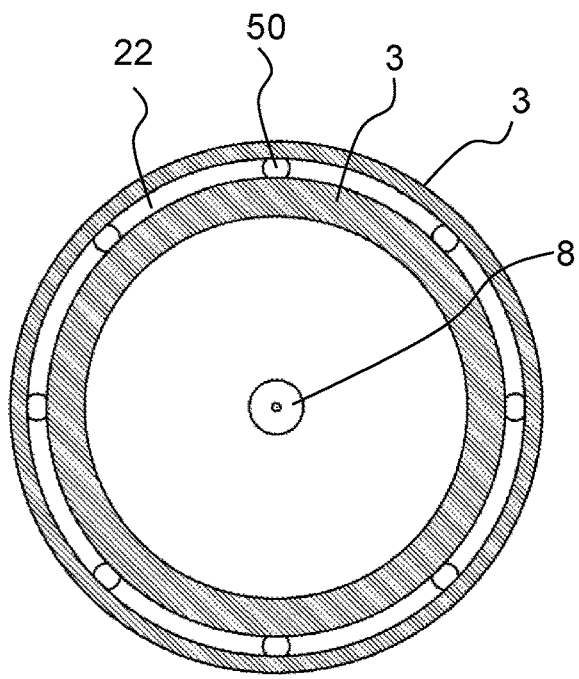
FIG. 19 shows a section through the embodiment according to FIG. 18 along A-A.
Figure 18:
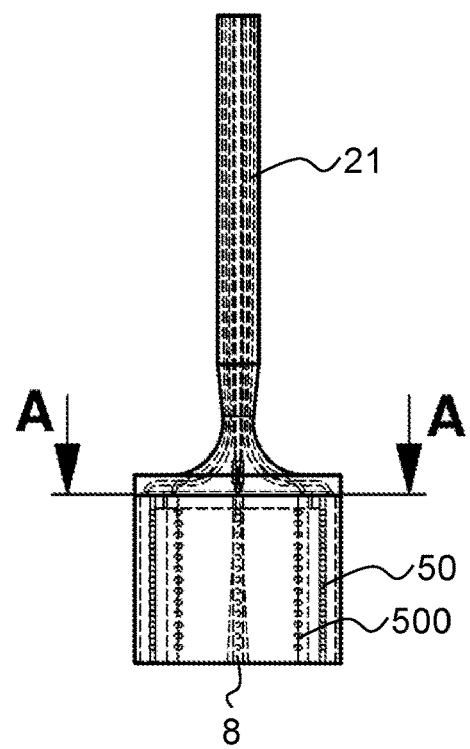
FIG. 18 shows a central sectional view of the embodiment according to FIG. 14.

In the embodiment according to FIGS. 14 and 15, radially extending suction channels 500 are present in addition to the axially extending suction channels 50. These radially extending suction channels 500 connect the axial suction channels 50 to the hollow interior 57 of the porous body 5, i.e. the space through which the fluid jet passes unimpeded. The radial suction channels 500 are preferably distributed along the entire length of the axial suction channels 50. The annular distributor channel 22 leading to the axial suction channels 50 can be seen clearly in FIGS. 18 and 19.

Figure 16:
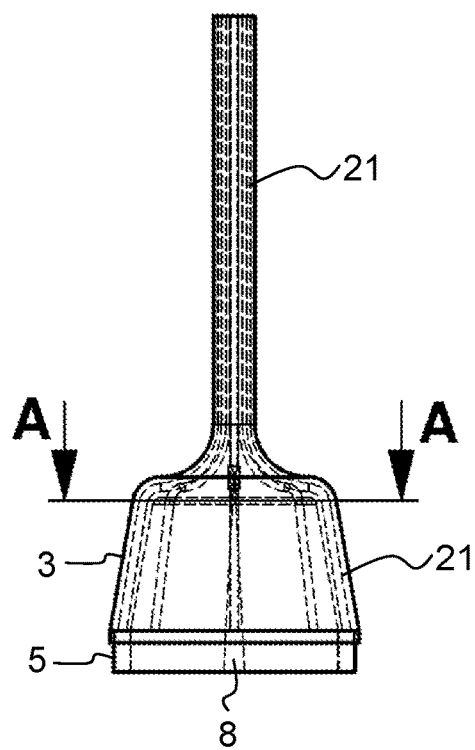
FIG. 16 shows a central sectional view of a further embodiment according to the invention with suction.
Figure 17:
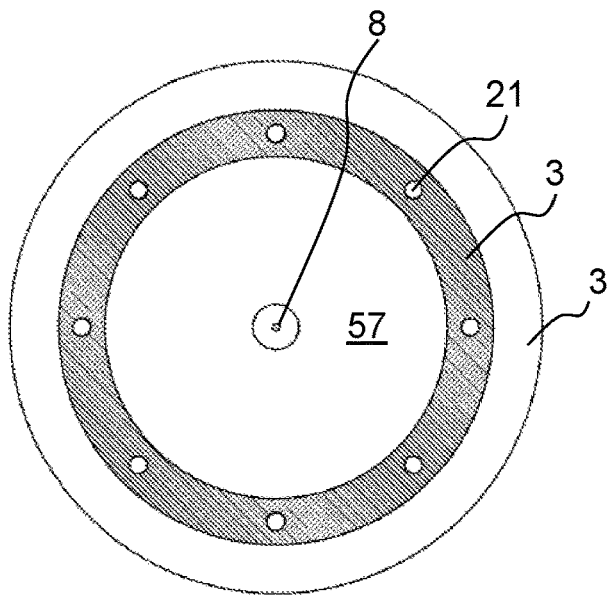
FIG. 17 shows a section through the embodiment according to FIG. 16 along A-A.

FIGS. 16 and 17 show a further embodiment. The suction channels 21 leading from the direction of the main body 2 extend through the front end 3 and open directly into the porous body 5. The front end 3 is relatively large and preferably has a conical shape widening toward the free end. The porous body 5 secured thereon has a cylindrical shape here and is relatively short in the jet direction.

Figure 20:
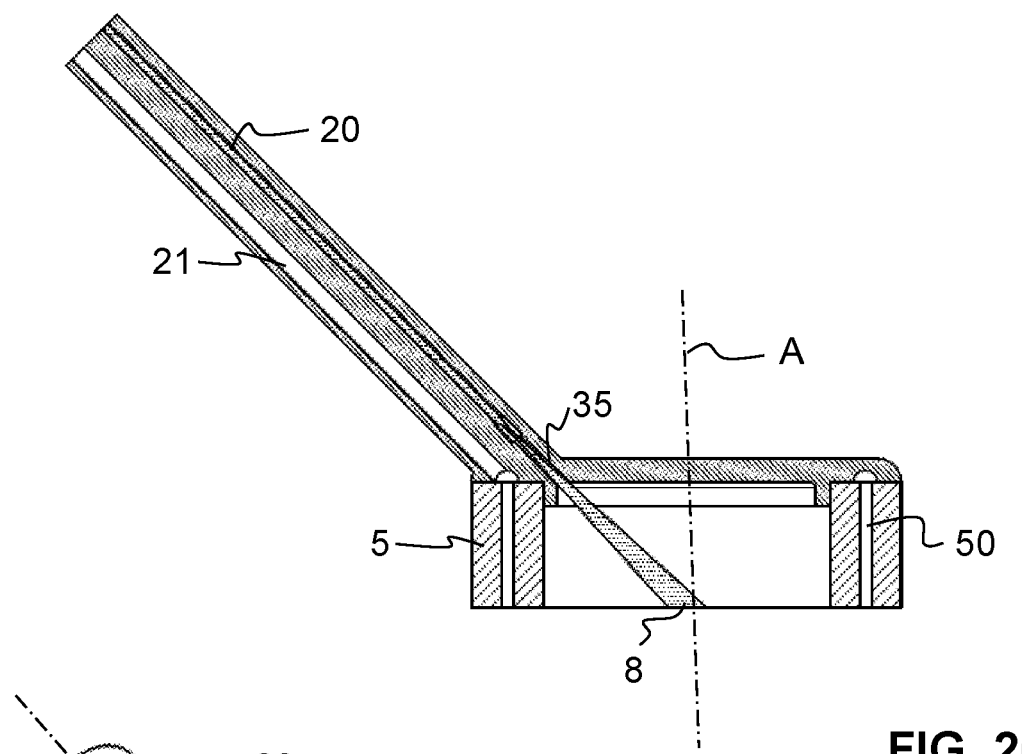
FIG. 20 shows a central sectional view of a further embodiment according to the invention.
Figure 21:
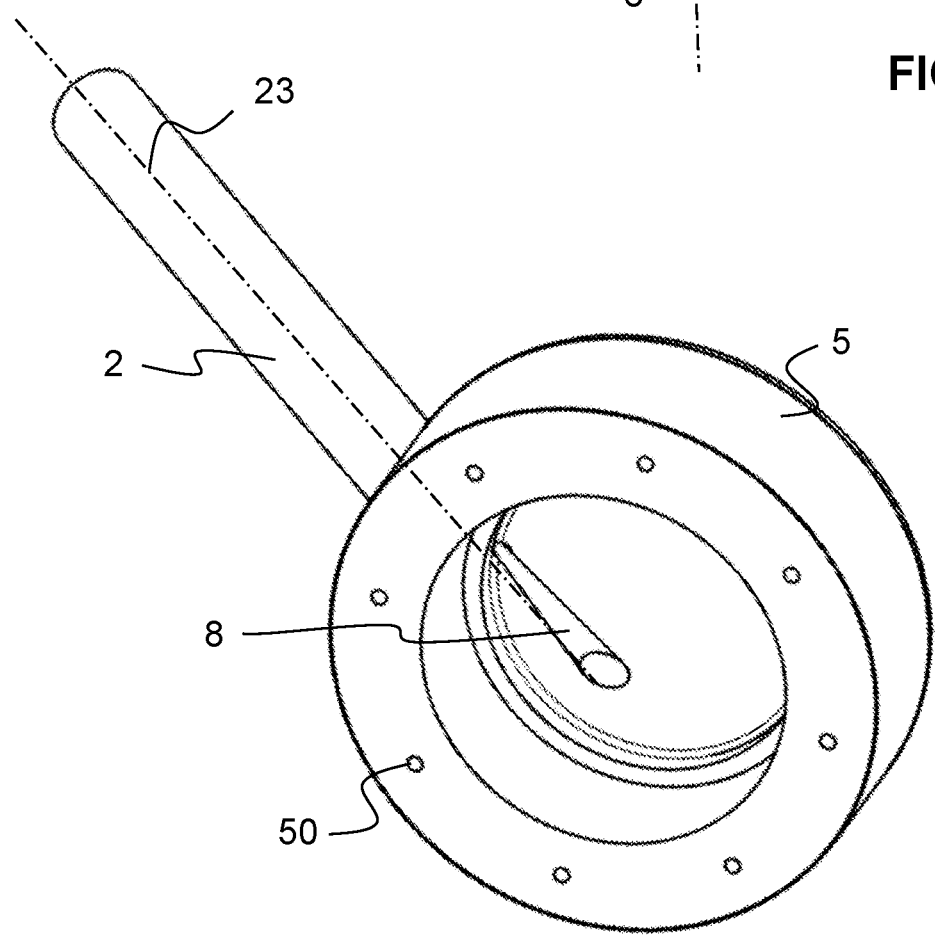
FIG. 21 shows a perspective view of the embodiment according to FIG. 20 from below.

In the embodiment according to FIGS. 20 and 21, the emergence opening 35 and the fluid channel 20 are oriented obliquely with respect to the longitudinal central axis A, such that the emerging fluid jet extends at an angle to the longitudinal central axis A. The angle is preferably approximately 45°. The hollow interior of the porous body 5 is preferably so dimensioned that the fluid jet does not strike an inner wall of the body. A suction system may be present. In other embodiments, no suction system is present. Moreover, the porous body can, as shown, have one or more axial and/or radial suction channels. In other embodiments, it has no suction channels. Otherwise, the features described for the other embodiments can also be used in an angled arrangement of the fluid jet. In particular, the porous bodies described above with their shapes and suction channels can also be used in this embodiment. In this example, only a single suction channel 21 is present in the handpiece 2 and opens into the annular distributor channel 22. However, it is also possible here for several suction channels 21 to be arranged in the handpiece 2.

The handpiece according to the invention combines the advantages of cleansing by a fluid jet with the advantages of mechanical cleansing and, at the same time, provides effective protection against aerosols.

What is claimed is:

1. A handpiece unit for cleansing wounds with a fluid jet, said handpiece unit comprising
    a fluid line being connected to a handpiece with a main body, the main body having a front end and a rear end, the fluid line being connected to the rear end of the main body, the fluid line ensuring a supply of pressurized fluid to the main body, the front end of the main body having a front face with an emergence opening for the emergence of a fluid jet of the pressurized fluid supplied by the fluid line, the handpiece provided with a nozzle arranged in the front end, the nozzle forming the emergence opening, a position of the nozzle being defined by a front abutment, the nozzle having a nozzle channel arranged centrally in the nozzle, wherein the design of the nozzle channel defines an emergence geometry of the fluid jet, the fluid jet emerging from the emergence opening being a microfluidic jet with a diameter of 0.05 mm to 0.15 mm,
    an adapter which is releasable connectable to the front end of the handpiece, the adapter surrounding and receiving the front end of the main body and surrounding the emergence opening,
    a porous body which is connected to the adapter, the porous body protruding beyond the emergence opening in a direction of a flow of the fluid jet emerging from the emergence opening,
    wherein the porous body defines a longitudinal central axis and wherein the direction of the fluid jet flowing out of the emergence opening extends inclined relative to the longitudinal central axis, the porous body having a through-opening, the through-opening forming a space through which the fluid jet flowing out of the emergence opening can pass unimpeded,
    wherein the porous body has a contact area for contact with a wound to be cleaned, which contact area extends perpendicularly with respect to the longitudinal central axis and which contact area extends at an angle other than 90 degrees with respect to the direction of the flow of the fluid jet emerging from the emergence opening,
    wherein the fluid jet flowing out of the emergence opening enters the through-opening of the porous body, wherein the fluid jet reaches an end of the through-opening, the end being surrounded by the contact area, wherein the fluid jet reaching the end of the through-opening reaches the longitudinal central axis, and
    wherein the adapter is transparent, permitting view of the wound to be cleaned.

2. The handpiece unit as claimed in claim 1, wherein the porous body is made of a sponge, fleece or knit like material.

3. The handpiece unit as claimed in claim 1, wherein the porous body has a hollow cylindrical, hollow conical or hollow polyhedral shape.

4. The handpiece unit as claimed in claim 1, wherein the porous body has, in the contact area, an outwardly directed, circumferential front collar.

5. The handpiece unit as claimed in claim 1, wherein the handpiece is stiff.

6. The handpiece unit as claimed in claim 1, wherein the porous body has pores and wherein suction channels are present in the porous body and wherein the suction channels have a diameter many times larger than an average pore size of the pores.

7. The handpiece unit as claimed in claim 6, wherein the suction channels extend in the direction of the longitudinal central axis and are rectilinear.

8. The handpiece unit as claimed in claim 6, wherein radially extending suction channels are present, which open into the space formed by the porous body.

9. The porous body and adapter as claimed in claim 1, wherein the porous body has radially and/or axially extending suction channels whose diameter is many times larger than the average pore size of its pores.

10. The handpiece unit as claimed in claim 1, wherein the porous body has an air-tight and liquid-tight outer skin which completely surrounds and covers an outer circumference of the porous body, the air-tight and liquid-tight outer skin being present during cleansing of the wounds.

11. The handpiece unit as claimed in claim 10, wherein the porous body has a lower face which is covered by the air-tight and liquid-tight outer skin.

12. The handpiece unit as claimed in claim 10, wherein the porous body has a lower face which is configured in an open-pored manner and which is free of the air-tight and liquid-tight outer skin.

13. A method for cleansing wounds with a handpiece unit, the handpiece unit cleansing wounds with a fluid jet, the handpiece unit comprising
    a handpiece with a main body, the main body having a front end, and a rear end,
    a fluid line being connected to the rear end of the main body, the fluid line ensuring a supply of pressurized fluid to the main body, the front end of the main body having a front face with an emergence opening for the emergence of the fluid jet of the pressurized fluid supplied by the fluid line, the handpiece provided with a nozzle arranged in the front end, the nozzle forming the emergence opening, a position of the nozzle being defined by a front abutment, the nozzle having a nozzle channel arranged centrally in the nozzle, wherein the design of the nozzle channel defines an emergence geometry of the fluid jet, the fluid jet emerging from the emergence opening being a microfluidic jet with a diameter of 0.05 mm to 0.15 mm,
    an adapter which is releasable connectable to the front end of the handpiece, the adapter surrounding and receiving the front end of the main body and surrounding the emergence opening, a porous body which is connected to the adapter, the porous body protruding beyond the emergence opening in a direction of a flow of the fluid jet emerging from the emergence opening, wherein the porous body defines a longitudinal central axis and wherein the direction of the fluid jet flowing out of the emergence opening extends inclined relative to the longitudinal central axis, the porous body having a through-opening, the through-opening forming a space through which the fluid jet flowing out of the emergence opening can pass unimpeded, wherein the porous body has a contact area for contact with a wound to be cleaned, which contact area extends perpendicularly with respect to the longitudinal central axis and which contact area extends at an angle other than 90 degrees with respect to the direction of the flow of the fluid jet emerging from the emergence opening, wherein the adapter is transparent, permitting view of the wound to be cleaned, and wherein the method comprises the steps of simultaneously cleansing the wound by the fluid jet emerging from the handpiece and treating the wound by the porous body arranged on the handpiece.

* * * * *

UNITED STATES PATENT AND TRADEMARK OFFICE
CERTIFICATE OF CORRECTION

PATENT NO. : 10,987,463 B2
APPLICATION NO. : 14/912772
DATED : April 27, 2021
INVENTOR(S) : Martin Schug et al.

Page 1 of 1

It is certified that error appears in the above-identified patent and that said Letters Patent is hereby corrected as shown below:

In the Claims

At Column 9, Line 44, "releasable" should be -- releasably --.

At Column 10, Line 64, "releasable" should be -- releasably --.

Signed and Sealed this
Tenth Day of August, 2021

Drew Hirshfeld
*Performing the Functions and Duties of the
Under Secretary of Commerce for Intellectual Property and
Director of the United States Patent and Trademark Office*